United States Patent [19]

Tanner

[11] Patent Number: 4,517,974
[45] Date of Patent: May 21, 1985

[54] DISPOSABLE HAND PIECE FOR SURGICAL LASERS

[75] Inventor: Howard M. C. Tanner, Salt Lake City, Utah

[73] Assignee: HGM, Inc., Salt Lake City, Utah

[21] Appl. No.: 437,289

[22] Filed: Oct. 28, 1982

[51] Int. Cl.³ .............................................. A61B 17/36
[52] U.S. Cl. ............................ 128/303.1; 128/303.14; 128/303.17
[58] Field of Search ...................... 128/303.1, 395–398, 128/303.13, 303.14, 303.17–303.19; 372/6, 108; 219/121 L, 121 LP

[56] References Cited

U.S. PATENT DOCUMENTS

| | | | |
|---|---|---|---|
| 3,467,098 | 9/1969 | Ayres | 128/303.1 |
| 3,471,215 | 10/1969 | Snitzer | 350/96 |
| 3,538,919 | 11/1970 | Meyer | 128/398 |
| 3,746,814 | 7/1973 | Lackey et al. | 200/157 |
| 3,821,510 | 6/1974 | Muncheryan | 219/121 L |
| 3,825,004 | 7/1974 | Durden, III | 128/275.1 |
| 3,865,113 | 2/1975 | Sharon et al. | 128/303.1 |
| 3,910,278 | 10/1975 | Crandell et al. | 128/303.1 |
| 3,974,833 | 8/1976 | Durden, III | 128/303.17 X |
| 3,982,541 | 9/1976 | L'Esperance, Jr. | 128/303.1 |
| 4,034,761 | 7/1977 | Prater et al. | 128/303.14 |
| 4,126,136 | 11/1978 | Auth et al. | 128/303.1 |
| 4,233,493 | 11/1982 | Nath | 219/354 |
| 4,316,467 | 2/1982 | Muckerheide | 128/303.1 |
| 4,427,006 | 1/1984 | Nottke | 128/303.14 |

FOREIGN PATENT DOCUMENTS

| | | | |
|---|---|---|---|
| WO82/02488 | 8/1982 | PCT Int'l Appl. | 128/303.14 |
| 858852 | 9/1981 | U.S.S.R. | 128/303.1 |

*Primary Examiner*—Edward M. Coven
*Attorney, Agent, or Firm*—B. B. Olive

[57] ABSTRACT

A disposable hand piece for attachment at the end of a laser catheter assembly. The hand piece is longitudinally tapered and is generally wedge-shaped in its width so as to form a tool which can be comfortable grasped by a surgeon for purposes of more accurately controlling the laser beam applied through the laser catheter. The hand piece includes an internal switching mechanism which may be conveniently activated by pressing flexible panels positioned on the sides of the hand piece. The hand piece is constructed of inexpensive plastic materials and is designed to be disposable after a single use.

2 Claims, 7 Drawing Figures

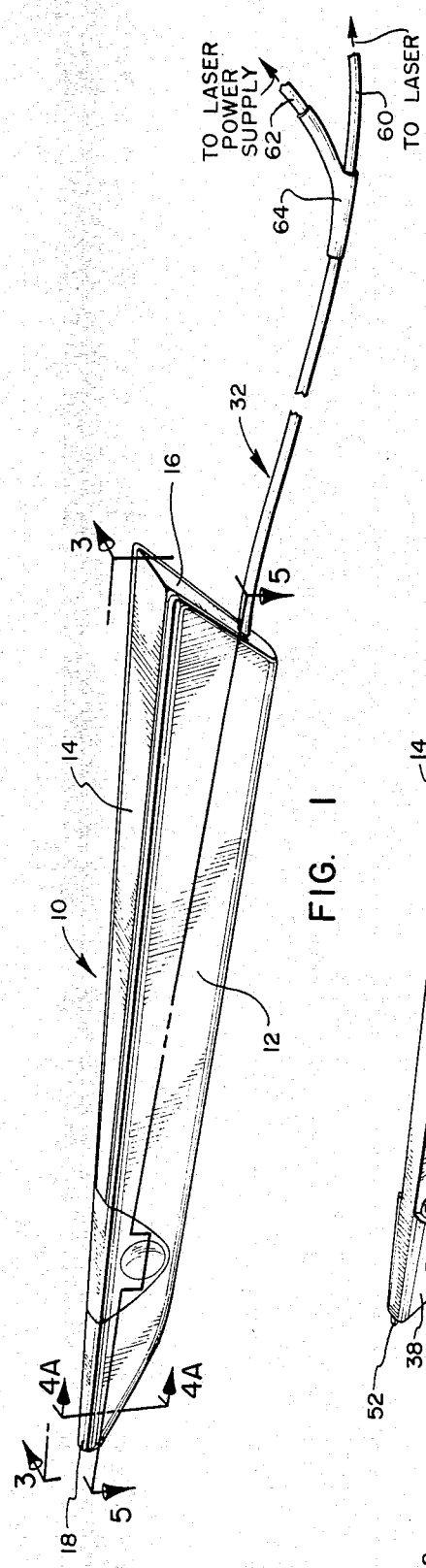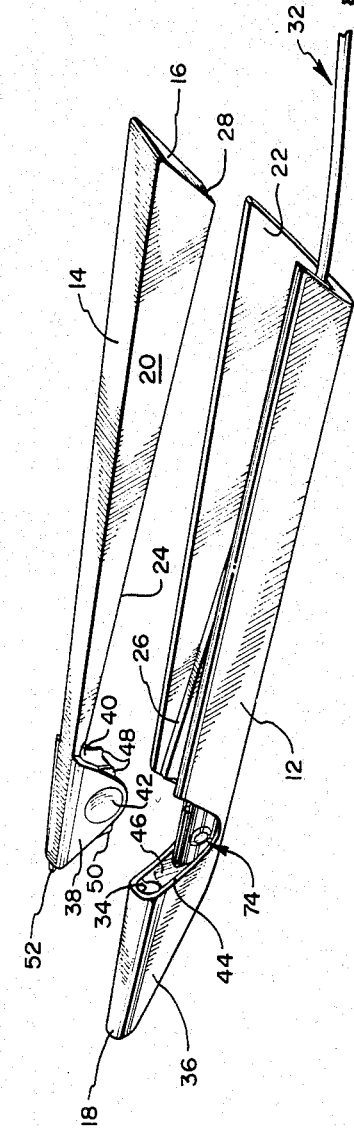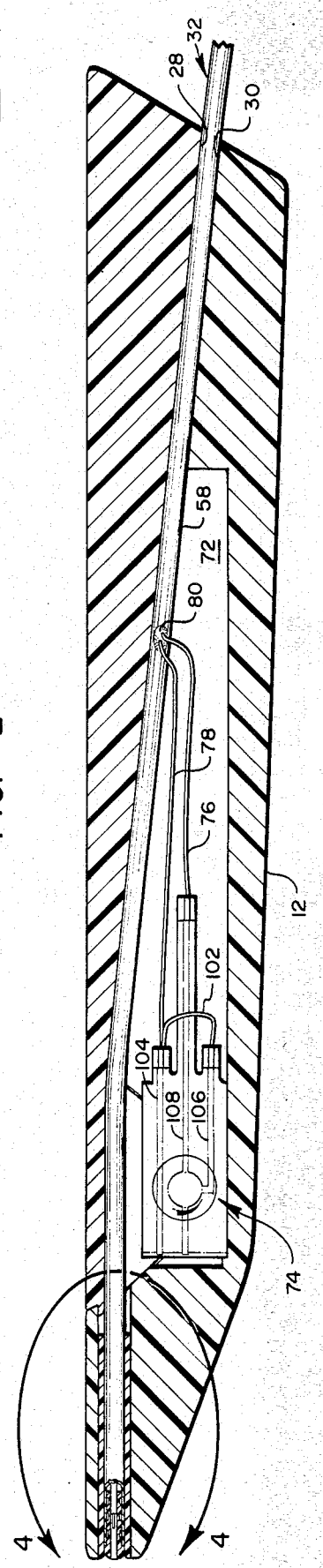

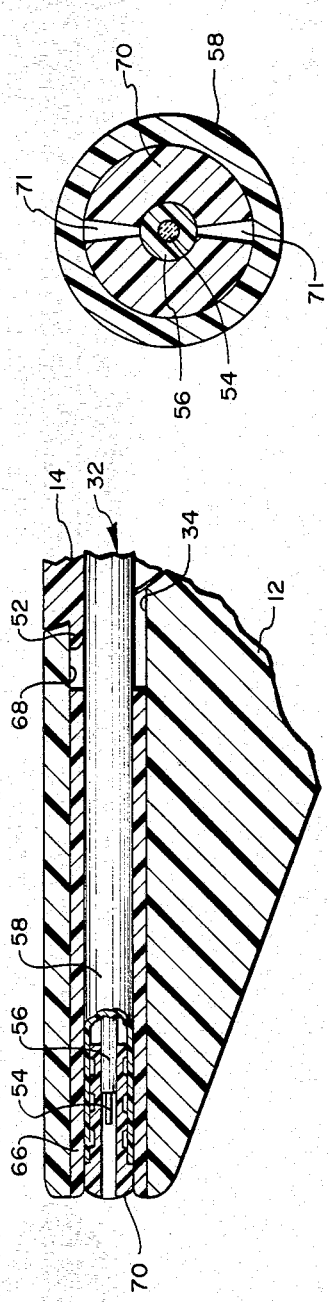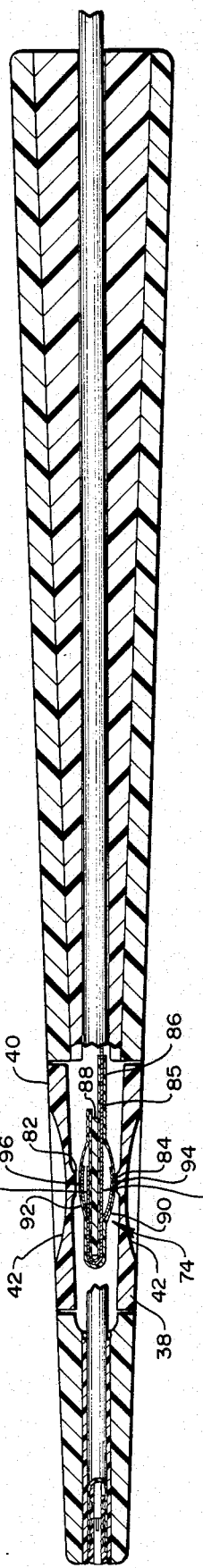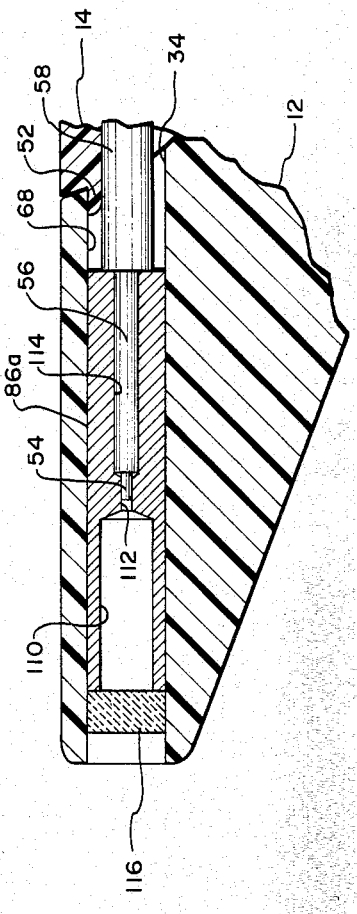

DISPOSABLE HAND PIECE FOR SURGICAL LASERS

BACKGROUND

1. The Field of the Invention

The present invention relates to surgical lasers and, more particularly, to a disposable hand piece which carries the optical fiber and electrical switching element of a surgical laser.

2. The Prior Art

Although the theory behind lasers was first described by Einstein in the early 1900s, it was not until several decades later that significant breakthroughs were made in their development. Early lasers utilized solid crystalline rods constructed, for example, from ruby. Such lasers were generally only capable of giving short bursts of light. In about 1958, scientists developed a process whereby laser light could be obtained by exciting various gases within a tube. This was a significant breakthrough since it meant that a continuous laser beam could be produced.

The advent of the laser has opened new frontiers to many areas of science and has revolutionized many procedures. One of the most important of these new frontiers has been the application of laser technology to various procedures in the field of medicine. The first significant medical use of a laser occurred in 1965 when doctors utilized an argon laser to repair a detached retina. The doctors were able to focus the laser into the interior portion of an eyeball and "weld" the detached retina back into place. Since that time, different types of lasers have been developed and applied to numerous surgical procedures.

For purposes of surgery, lasers operate on the principle that the highly collimated laser light beam may be converted into thermal energy when focused upon tissue. Because lasers can be focused onto very small areas, it is possible to be extremely precise during certain operations and to treat specific pathologies without affecting surrounding tissue. Each type of laser produces a light beam having a specific and unique wave length. Inasmuch as different wave lengths of light are absorbed, reflected, scattered, or transmitted by tissue to varying degrees, each type of laser has been found to have unique applications.

For example, argon lasers produce a visible blue-green light having a wavelength in the 488 to 514 nanometer range. This light is easily transmitted through clear aqueous tissues such as the cornea, lens and vitreous humor of the eye. On the other hand, certain tissue pigments such as melanin and hemoglobin absorb this light very effectively. Therefore, argon lasers have proven to be very effective in treating pigmented lesions such as port-wine hemangiomas. The laser light passes through the skin surface without being absorbed significantly until it reaches the pigmented layer where it is almost totally absorbed, causing heat generation and protein coagulation.

The argon laser can also effectively be utilized as a scalpel. By focusing the laser to a narrow beam or by increasing its intensity, the power density can be increased to a strength sufficient to vaporize the target tissue, thus allowing incisions to be made. Additionally, because the argon-produced light is readily absorbed by hemoglobin, severed blood vessels are coagulated simultaneously with the formation of the incision.

A second type of laser which has found significant use in the medical field is the carbon dioxide ($CO_2$) laser. The $CO_2$ laser produces invisible infrared light with a wave length of about 10,600 nanometers. This light is entirely absorbed by the water present in body tissues within about 100 microns of the point of impact. However, because of this efficient absorption, $CO_2$ lasers make effective scalpels but must be used in dry, non-bleeding areas to prevent the energy from being dispersed. Because the $CO_2$ light beam is so readily absorbed, it cannot be used when it is necessary to transmit the light through various layers of tissue to reach the pathology.

Other types of lasers which have been utilized in surgical procedures include the neodymium yttrium aluminum garnet (Nd-YAG) and xenon lasers. Each of these lasers also has its preferred applications.

Some laser beams such as those of the argon, Nd-YAG, and xenon lasers can be transmitted through optical fibers to the point of application. On the other hand, because the $CO_2$ laser has a relatively large wavelength, it cannot be transmitted through these optical fibers but must be directed through multi-jointed arms containing lenses and mirrors, and is thus limited to line of sight operations. Additionally, the multi-jointed arms with their accompanying lenses and mirrors are complicated and expensive to construct. Accordingly, argon type lasers are more convenient to use and they have found a wide variety of applications in the medical field.

The optical fiber (typically quartz) used to transmit an argon-type laser beam may be extremely small, generally ranging from about 0.1 to about 0.6 millimeters in diameter, and is quite fragile. Accordingly, the fiber is usually encased within a silicon sheath and is then placed within some type of protective plastic tubing. The entire assembly is sometimes referred to as a "laser catheter."

In the past, it has been common practice for surgeons to simply grasp the protective tubing when using an argon type laser in surgical procedures. This may create some difficulties because the tube is very flexible and long, and is thus difficult to control with a high degree of precision. Moreover, because the optical fiber is sometimes very small, the overall protective tubing may also be correspondingly small in size and thus, difficult to grasp near the tip when attempting to position the tip of the optical fiber with precision.

Another common problem in the state of the art is that argon type medical lasers typically do not have a convenient means for switching the laser on and off. A small amount of light is generally constantly transmitted through the optical fiber for purposes of assisting the surgeon to accurately aim the laser beam. However, because of the extreme power of the laser beam, it is imperative that full power only be applied at the precise instant that the surgeon desires to perform the surgical procedure. Normally, full laser power is controlled by a foot switch connected to the laser source.

The use of a foot switch for purposes of turning the laser beam on and off gives rise to several disadvantages. First, the surgeon must be very careful that he does not accidentally activate the foot switch. Second, in many types of operations the surgeon will be required to operate over substantial periods of time, which will mean repeated activation and deactivation of the laser foot switch. During this type of extended operation, the surgeon may become extremely uncomfortable or fatigued by virtue of the fact that he must constantly keep one foot resting on the foot switch, which prevents him from putting his full weight on that foot. Obviously, this may adversely affect the surgeon's balance, rendering his job more difficult. Moreover, if the surgeon completely removes his foot from the foot switch, the switch may become displaced and he may have difficulty locating it once it is desired to again activate the laser beam. This is especially disadvantageous should the surgeon unexpectedly need to utilize the laser beam to coagulate bleeding vessels. Finally, it is also difficult to control the foot switch, especially when wearing shoes. Use of a foot switch also renders it more difficult for the surgeon to accurately place a laser beam and requires additional hand and foot coordination, which greatly increases the difficulty of the surgical procedure.

Accordingly, what is needed in the art is a hand piece which can be attached to the end of a laser catheter assembly so as to provide the surgeon with a convenient tool which he can easily grasp and which he can more easily and more precisely use for purposes of positioning the tip of the optical fiber, and which includes means for activating or deactivating by hand the laser beam supplied through the catheter assembly.

OBJECTS AND BRIEF SUMMARY OF THE INVENTION

It is a primary object of the present invention to provide a hand piece which can be attached to the end of a laser catheter assembly to facilitate handling.

It is a further object of this invention to provide a hand piece which includes means for conveniently activating by hand the laser source to which the laser catheter assembly is attached.

Another object of this invention is to provide a laser hand piece which is sufficiently economical in its construction as to be completely disposable after each use, thus eliminating the need for time consuming and costly resterilization techniques.

These and other objects and features of the present invention will become more fully apparent from the following description and appended claims taken in conjunction with the accompanying drawings.

In accordance with the foregoing objects, the present invention provides a novel, disposable hand piece which can be attached to the end of a laser catheter assembly to assist a surgeon in directing and operating the laser.

In one preferred embodiment, the apparatus of the present invention comprises an elongated hand piece having a generally tapered, wedge-shaped configuration which is adapted to be comfortably held in the hand in a pencil-like manner. A conduit is formed through the length of the hand piece into which the laser catheter assembly is positioned. A pair of electrical wires are inserted into the laser catheter assembly and are attached to a membrane switch positioned in the forward portion of the hand piece. The switch is positioned between two flexible, resilient panels, each forming a portion of the side of the hand piece. Thus, the hand piece can comfortably be held in the surgeon's hand and the tip can be directed to the point where the laser is to be applied. The surgeon can then gently squeeze the flexible panels to activate the laser.

Additionally, the laser hand piece includes an interchangeable sleeve in the forward portion thereof. The sleeve is used to securely anchor the end of the laser catheter assembly in the hand piece. The sleeve may include a lens or collimator to increase the focusing of the laser beam with greater precision.

The entire hand piece is designed to be easily and inexpensively fabricated such that it can be disposed of together with the entire laser catheter assembly after a single use.

BRIEF DESCRIPTION OF THE DRAWINGS

Reference is next made to the drawings, in which like parts are designated with like numerals throughout, and in which:

FIG. 1 is a perspective view of a laser hand piece constructed in accordance with the present invention;

FIG. 2 is an exploded perspective view of the laser hand piece of FIG. 1;

FIG. 3 is an enlarged cross-sectional view of a first preferred embodiment of the present invention taken along line 3—3 of FIG. 1;

FIG. 4 is an enlarged view of the front portion of the cross-section encompassed by line 4—4 illustrated in FIG. 3;

FIG. 4a is an enlarged end-sectional view of the tip of the laser catheter used in conjunction with the laser hand piece of the present invention taken along lines 4A—4A of FIG. 1;

FIG. 5 is an enlarged cross-sectional view of the first preferred embodiment of the laser hand piece of the present invention taken along lines 5—5 of FIG. 1; and FIG. 6 is an enlarged cross-sectional view of the front portion of a second preferred embodiment of the present invention.

DETAILED DESCRIPTION OF THE PREFERRED EMBODIMENTS

Referring first to FIG. 1, a laser hand piece constructed according to the present invention is generally designated at 10. As shown in FIGS. 1 and 2, the laser hand piece 10 includes body portion 12 and a cap portion 14 which are designed to to be snapped and bonded together as hereinafter more fully described. The hand piece 10 is generally tapered from the trailing end 16 up to the tip or leading end 18. As illustrated in FIG. 2, in addition to the taper, the cap portion 14 of hand piece 10 is also wedge-shaped and is thus also tapered inwardly on the longitudinal sides 20 thereof. The body portion 12 of hand piece 10 has a corresponding V-shaped channel 22 which is adapted to receive the wedge-shaped cap portion 14. Longitudinal sides 20 of the cap portion 14 are also designed with an inclining edge 24 which is supported by a corresponding inclined shoulder 26 formed along the inside surface of the V-shaped channel 22.

As shown at the trailing end 16 of the cap portion 14, a groove 28 is formed along the underside of the cap portion 14 along its entire length (see also FIG. 3) from one end thereof to the other. A corresponding groove 30 (see FIG. 3) is also formed at the bottom of the V-shaped channel 22 in the body 12 of the hand piece 10. When the cap 14 and body 12 are joined together as in FIGS. 1 and 3, grooves 28 and 30 form a conduit through which a laser catheter assembly generally designated at 32 enters the hand piece 10 at the trailing end 16 thereof. As shown best in FIG. 3, the laser catheter assembly 32 rests in the groove 28 formed in the underside of cap portion 14 and projects into the bore 34 (see FIG. 2) which is located through the front portion 36 of the body 12. As can be seen, the front portion 36 of body 12 slopes upwardly so as to form a pencil-like tip 18 at the forward portion of the hand piece 10.

With further reference to FIGS. 1 and 2, the cap portion 14 also includes a pair of flexible panels 38 and 40 which extend downwardly along the sides of the cap portion 14. As hereinafter more fully described, the flexible panels 38 and 40 are designed so as to be resilient and so as to be slightly biased outwardly so that when the panels 38 and 40 are squeezed by the fingers, an electrical switch will be activated which turns on the laser beam. Each of the flexible panels 38 and 40 include a generally circular indentation 42 on the face thereof. The indentations 42 are adapted to comfortably receive the fingers so that the fingers may be firmly positioned on the flexible panels 38 and 40, which form the external switch mechanism or trigger of the laser hand piece 10.

Body 12 is provided with corresponding notches 44 and 46 along the sides thereof which receive the flexible panels 38 and 40. Flexible panels 38 and 40 are also provided with two small tabs 48 and 50 (see FIG. 2) and the leading end of the cap portion 14 is provided with a similar tab 52. The tabs 48, 50 and 52 are designed to be inserted along the inside edges of the notches 44, 46 and bore 34, respectively. The tabs 48, 50 and 52 are thus used to snap the tip and flexible panels 38 and 40 of cap portion 14 onto the body 12. The rear of cap portion 14 may be glued or otherwise suitably bonded to the inclined shoulder 26 and/or the sides of the V-shaped channel 22 of body 12, so as to form a completely enclosed, integral hand piece.

In the illustrated embodiment, cap portion 14 and body 12 of hand piece 10 are constructed from high impact styrene which are formed as molded components using conventional molding techniques. Of course, other suitable materials could work equally as well.

As best illustrated in FIG. 4, the laser catheter assembly 32 includes an optical fiber 54 which forms the center of the laser catheter 32. The optical fiber 54 is a 600 micron quartz fiber having a bend radius of approximately 2 cm. The optical fiber 54 is encased by silicon cladding 56 which enhances the optical transmission properties of fiber 54 and which also forms a protective sheath around the optical fiber 54 so that the fiber, which is otherwise quite brittle, will be protected from damage. In some cases, an additional layer (not shown) of Tefzel (TM) may also be used to further strengthen the quartz fiber 54. The optical fiber 54 and the silicon cladding 56 are typically referred to in the art as "dressed optical fiber," which may be readily obtained from a number of commercial manufacturers. For example, in the illustrated embodiment the dressed optical fiber may be obtained from Quartz Products Co. of Plainfield, N.J.

With continuing reference to FIG. 4, the dressed optical fiber consisting of quartz fiber 54 and silicon cladding 56 is inserted through a radially enlarged polyethylene conduit 58. The diameter of conduit 58 is large enough so as to provide a space around the dressed optical fiber, thus permitting a cooling gas such as carbon dioxide to be forced through the conduit 58 and out the tip of the laser hand piece. The carbon dioxide gas is used to cool the tip of the optical fiber and is also used to disperse any vaporized tissue that may tend to collect on the tip of the fiber.

As shown in FIG. 1, the laser catheter assembly 32 is attached at one end 60 thereof to a laser (not shown) and to a source of pressurized carbon dioxide gas (not shown). In the illustrated embodiment the laser may be, for example, an argon ion type laser. Other suitable kinds of lasers could also be used. The laser catheter assembly 32 also includes a second conduit 62 which, as hereinafter more fully described, carries a pair of electrical wires which lead to the power supply (not shown) of the laser and which are used to selectively activate or deactivate the laser beam for purposes of the surgical procedure to be performed. The conduit 62 is joined to the laser catheter assembly 32 by means of a conventional heat shrink wrap 64.

With reference again to FIG. 4, the other end of the laser catheter assembly 32 terminates in a cylindrical sleeve 66 which is inserted in the bore 34 at the tip 18 of body 12. The sleeve 66 is slightly shorter in length than the bore 34, thus leaving a small space 68 at the end of bore 34 which is adapted to receive the tab 52 which is used to help snap the cap portion 14 onto the body 12 of the hand piece. As further illustrated in FIG. 4, the optical fiber 54 is bared at its leading end and projects into a collet 70 which is inserted into the leading end of the conduit 58. As shown best in the enlarged end-sectional view of FIG. 4a, collet 70 has a plurality of slits 71 running from the back end thereof to a point slightly beyond the tip of fiber 54 to allow the carbon dioxide gas to pass therethrough and to exit near the bare tip of the fiber 54 for purposes of cooling as described above.

Reference is next made to FIGS. 3 and 5, which illustrate in greater detail the switch mechanism of the laser hand piece. Referring first to FIG. 3, the body 12 has an elongated, enlarged channel 72 formed in the interior thereof. Elongated channel 72 is adapted to receive the membrane switch generally designated at 74, which is positioned inside of the body 12. Elongated channel 72 is long enough to accommodate the electrical connections and wires 76 and 78 which are connected to the switch 74 and which are introduced through the conduit 58 of the laser catheter assembly. Wires 76 and 78 are inserted through a small hole 80 which may thereafter be enclosed by a small globule of silicon (not shown) or by a conventional heat shrink sleeve (not shown).

The switch 74 consists of a plastic membrane switch which may be activated from either side of the laser hand piece by squeezing at circular indentations 42 on the flexible panels 38 or 40. As shown best in the sectional top view of FIG. 5, the flexible panels 38 and 40 each include on their inside surface a small, raised bump 82 and 84 which just barely contacts or is slightly separated from the sides of the membrane switch 74. The membrane switch 74 consists of two elongated pieces of plastic 85–86 which are bonded together and which are folded around a rigid, upright post 88 formed at the center and as an integral part of the interior of body 12. The outer layer of plastic 86 is resilient and is formed with raised domes 90 and 92 which have metal contacts 94 and 96 positioned on the inside surface thereof. The metal contacts 94 and 96 are designed to engage corresponding metal contacts 98 and 100 which are positioned on the outside surface of the second layer of plastic 85. Thus, when the indentations 42 of the flexible panels 38 or 40 are squeezed inwardly metal contacts 94 or 96 engage the corresponding metal contacts 98 or 100, switching on the laser beam by means of wires 76 and 78 which are connected to the laser power supply (not shown).

As shown in FIG. 3, the contact pair 96 and 100 are connected by a thin conductive strip 104 which in turn is connected to wire 78. The contact pairs 94, 98 are likewise electrically connected through a conductive strip 106 and through wire 102 to wire 78. Wire 76 is connected through conductive strip 108 to both pairs of contacts so that by making contact on either side of the hand piece the laser beam can be activated. In the illustrated embodiment the membrane switch may be manufactured using conventional technology, and is available from Rogers Corporation of Tempe, Ariz.

Advantageously, by providing for activation of the laser beam on either side of the laser hand piece, better control is accomplished and the laser hand piece is much more convenient to use. The tapered, wedge-shape of the hand piece also facilitates greater accuracy and control of the laser beam because the hand piece is designed to fit comfortably within the surgeon's hand in a pencil-like fashion. Thus, less fatigue results over extended periods of use using the hand piece of the present invention. Also, since the trailing end 16 of the hand piece slopes inwardly and also because the laser catheter 32 is directed on an incline, the laser catheter slopes down and away so as to be out of the way of the surgeon as the hand piece is used. The hand piece is very light in weight and is easily constructed, further adding to its convenience and also its very economical construction which accommodates disposal after a single use.

Reference is next made to FIG. 6, which illustrates an additional feature of the laser hand piece of the present invention. In FIG. 6, the body, cap and switching means are identical to that previously described in connection with FIGS. 1-5. Only the cylindrical insert sleeve positioned in the forward end of the conduit 58 is different.

As shown in FIG. 6, the sleeve 86a has an enlarged bore 110 at the forward end thereof. The enlarged bore 110 communicates with a diameterally-reduced central bore 112 in which the bared, leading end of optical fiber 54 is positioned. The central bore 112 in turn communicates with a somewhat larger bore 114 through which the optical fiber 54 and silicon cladding 56 extends. At the leading end of the sleeve 86a a collimator in the form of a lens 116 is positioned. In this particular embodiment, carbon dioxide or other inert gas is not forced through the conduit 58 inasmuch as the sleeve 86a is enclosed at its end by the lens 116. Lens 116 may be desirable in applications where it is necessary to focus the laser beam with greater precision.

In summary, from the foregoing description it will be appreciated that the laser hand piece of the present invention is simple and inexpensive to construct so that it may be readily disposed of together with the laser catheter assembly after a single use. Further, the design of the hand piece is such that it provides a comfortable tool for the surgeon to work with. The laser hand piece is much more convenient to operate because it permits the surgeon to activate the laser by means of a simple hand movement applied at the sides of the hand piece, as opposed to the prior state of the art which employed a cumbersome and difficult to use foot switch.

It should further be appreciated that while the present invention has been particularly described in reference to the presently preferred embodiments, the invention may be embodied in other specific forms without departing from its spirit or essential characteristics. Thus, the described embodiments are to be considered in all respects only as illustrative and not restrictive. The scope of the invention is, therefore, indicated by the appended claims rather than by the foregoing description, and all modifications or changes which come within the meaning and range of equivalency of the claims are to be embraced within their scope.

What is claimed and desired to be secured by United States Letters Patent is:

1. A disposable hand piece for controlling and directing the application of a laser beam produced by a laser powered by an electrical power source and transmitted through an optical fiber connected to said laser and encased in a sheath, comprising:
   (a) an elongated body having a leading end and a trailing end, comprising:
      (i) a plastic molded top portion having a pair of opposed resiliently outwardly biased side panels at the leading end thereof;
      (ii) a plastic molded bottom portion having a pair of notches formed in opposed sides thereof for receiving said side panels, said top portion being shaped to nest in said bottom portion behind the leading end thereof;
      (iii) said top and bottom portions being secured together to form said body and providing:
         (aa) a bore extending through said body, said optical fiber encased by said sheath being mounted in said bore;
         (bb) a cavity within said body intermediate the length thereof; and
         (cc) in a leading portion of said bottom portion forward of said cavity, means anchoring the leading end of said optical fiber encased by said sheath; and
   (b) a pressure-sensitive switch mounted in said cavity between said panels and including electrical contacts positioned for being actuated by depressing either of said panels inwardly while holding said hand piece; and
   (c) electrical leads extending from said switch through said sheath encasing said optical fiber and branching from said sheath to said power source enabling said laser beam to be switched on and off by means of depressing either of said panels to actuate said switch while holding said hand piece.

2. A disposable hand piece as claimed in claim 1 wherein:
   (a) said bore is downwardly sloped toward said trailing end to cause said sheath with said encased optical fiber to drape downwardly from the trailing end of said hand piece body; and
   (b) as viewed in both elevation and plan, said body is shaped to taper from said trailing to said leading end.

* * * * *